United States Patent [19]
Amtower

[11] Patent Number: 5,395,621
[45] Date of Patent: Mar. 7, 1995

[54] APPARATUS AND METHOD FOR DISINFECTING A CONTACT LENS AND DETECTING THE PRESENCE OF AN OXIDATIVE DISINFECTANT

[75] Inventor: Patricia C. Amtower, Dana Point, Calif.

[73] Assignee: Allergan, Inc., Irvine, Calif.

[21] Appl. No.: 909,727

[22] Filed: Jul. 7, 1992

Related U.S. Application Data

[63] Continuation-in-part of Ser. No. 796,902, Nov. 22, 1991, which is a continuation of Ser. No. 588,085, Sep. 25, 1990, abandoned.

[51] Int. Cl.$^6$ .............................................. A61K 33/40
[52] U.S. Cl. .................................... 424/613; 514/912
[58] Field of Search ......................... 424/613; 514/912

[56] References Cited

U.S. PATENT DOCUMENTS

| Re. 32,672 | 5/1988 | Huth et al. | 252/95 |
|---|---|---|---|
| 3,183,173 | 5/1965 | Oakes | 195/103.5 |
| 3,694,384 | 9/1972 | Factor et al. | 260/2.2 R |
| 3,910,296 | 10/1975 | Karageozian et al. | 134/2 |
| 4,283,491 | 8/1981 | Dappen | 435/10 |
| 4,295,851 | 10/1981 | Neumann et al. | 8/524 |
| 4,521,375 | 6/1985 | Houlsby | 422/29 |
| 4,568,517 | 2/1986 | Kaspar et al. | 422/30 |
| 4,670,178 | 6/1987 | Huth et al. | 252/95 |
| 4,851,353 | 6/1989 | Miike et al. | 436/71 |

FOREIGN PATENT DOCUMENTS

WO860569 5/1986 WIPO.
WO9204921 4/1992 WIPO.
WO9204922 4/1992 WIPO.

OTHER PUBLICATIONS

Sheu et al, "Iron–Induced Activation of Hydrogen Peroxide for the Direct Ketonization of Methylenic Carbon [c–$C_6H_{12}$ c–$C_6H_{10}$(O)] and the Dioxygenation of Acetylenes and Arylolefins," American Chemical Society 1990.

Alexandratos et al, "Synthesis and Characterization of Bifuncational Ion–Exchange/Coordination Resins, Macromolecules" 1987, 20, 1191–1196.

Sheu et al, "Iron–Hydroperoxide–Induced Phenylselenization of Hydrocarbons (Fenton Chemistry)", American Chemical Society 1989.

Alexandratos et al, "Dual Mechanism Bifunctional Polymers: Polystyrene–Based Ion–Exchange/Redox Resins", American Chemical Society 1986.

Mazur et al, "Integration of Fundamental Polymer Science and Technology" (1986).

*Primary Examiner*—Zohreh Fay
*Attorney, Agent, or Firm*—Frank J. Uxa

[57] ABSTRACT

An apparatus and method useful for disinfecting a contact lens are disclosed. The apparatus includes a color indicator component comprising a transition metal component and a polymeric matrix material. This transition metal component, which is immobilized on the polymeric matrix material, provides a color indication of the presence of the oxidative contact lens disinfectant, e.g., hydrogen peroxide, in a liquid medium.

15 Claims, 1 Drawing Sheet

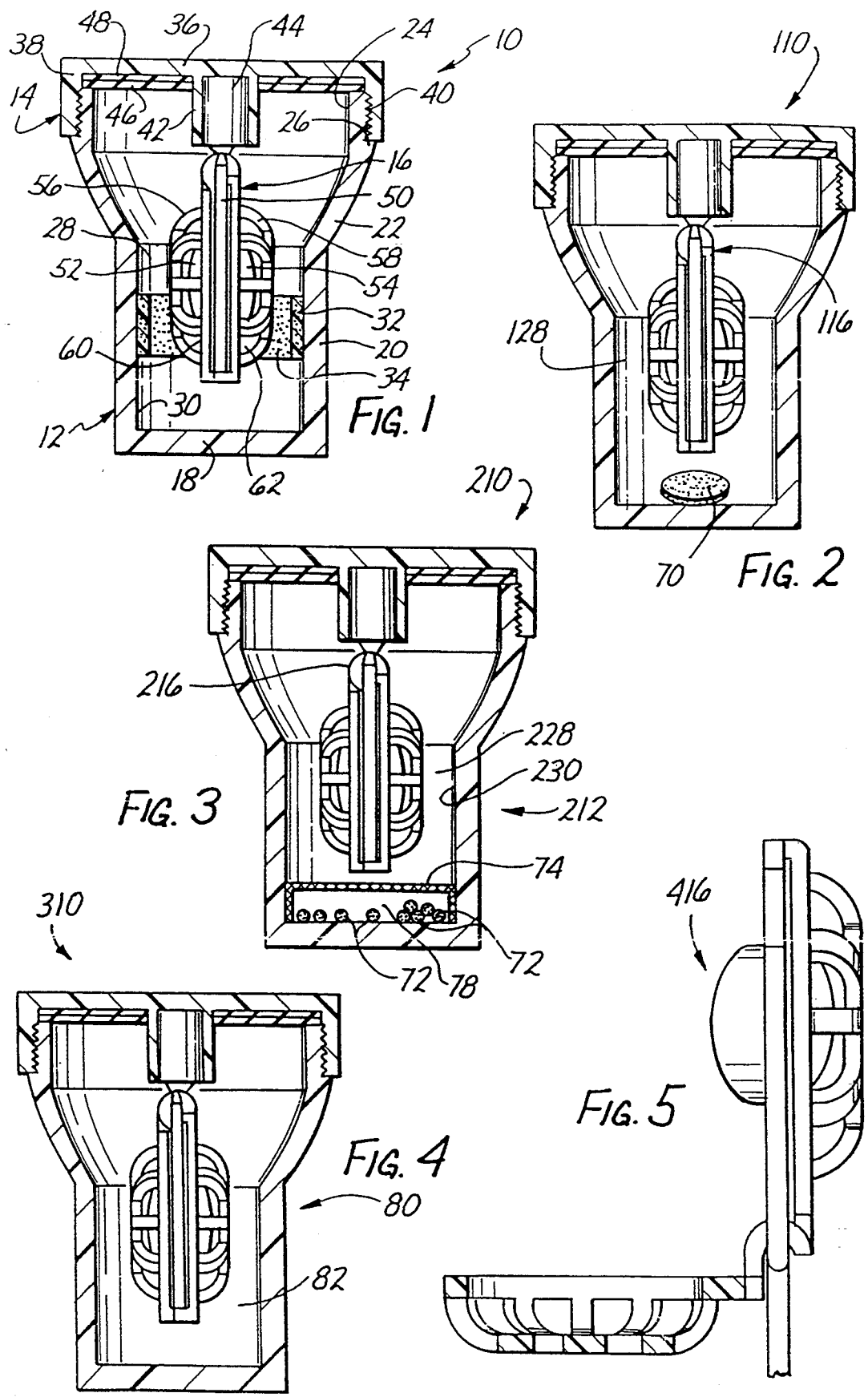

APPARATUS AND METHOD FOR DISINFECTING A CONTACT LENS AND DETECTING THE PRESENCE OF AN OXIDATIVE DISINFECTANT

RELATED APPLICATIONS

This application is a continuation-in-part of application Ser. No. 796,902, filed Nov. 22, 1991, now pending, which, in turn, is a continuation of application Ser. No. 588,085, filed Sep. 25, 1990, now abandoned.

BACKGROUND OF THE INVENTION

The present invention relates to an apparatus and method useful for disinfecting a contact lens. More particularly, this invention relates to such an apparatus and method in which the presence of, and preferably the substantial absence of, an oxidative disinfectant is indicated.

Contact lenses should be periodically disinfected by the user to prevent infection or other deleterious effects on ocular health which may be associated with contact lens wear. Currently, there are several different conventional systems and methods which enable the user to disinfect his/her contact lenses between wearing times. These conventional cleaning and disinfection systems can be divided into "hot" and "cold" systems. Hot systems require the use of heat to disinfect the contact lenses, whereas cold systems use chemical disinfectants at ambient temperatures to disinfect the lenses.

Within the realm of cold disinfection systems are oxidative disinfectant, in particular hydrogen peroxide, disinfection systems. Disinfecting hydrogen peroxide solutions are effective to kill the bacteria and fungi which may contaminate contact lenses. However, residual hydrogen peroxide on a disinfected contact lens may cause irritation, burning or other trauma to the eye unless this hydrogen peroxide is destroyed, i.e., decomposed, neutralized, inactivated or chemically reduced. Therefore, destruction of the residual hydrogen peroxide in the liquid medium containing the disinfected contact lens is needed to enable safe and comfortable wear of the disinfected contact lens.

In order to avoid trauma to the eye caused by the presence of oxidative disinfectant on or in the lens, it would be advantageous to have an indication of the presence of such oxidative disinfectant. Additionally, it would be advantageous to have an indication of the substantial absence of such oxidative disinfectant, e.g., so that one would know it was safe to place the disinfected lens into one's eye.

A number of soluble color indicators have been suggested for use in contact lens disinfecting service. See, for example, Huth et al U.S. Pat. No. 4,670,178 and Davies et al U.S. Pat. No. 4,863,627. The use of soluble color indicators has certain disadvantages. For example, the soluble color indicator comes into intimate contact with the contact lens being treated and may have a detrimental effect on the lens and/or on the wearer of the lens. Also, such soluble color indicators are discarded with the disinfecting solution after each disinfection cycle. This "one time" use of color indicators increases the cost of this safety feature.

Color indication or indications of the presence and absence of hydrogen peroxide should be clear and distinct. Also, intimate contact between the lens being disinfected and the color indicator component should be avoided so that the lens and the lens wearer are not adversely affected by the color indicator component. Further, since contact lenses are repeatedly disinfected, the color indicator component should be such as to repeatedly provide the desired color indication or indications in a reliable and reproducible manner.

There continues to be a need for a contact lens care system which effectively disinfects a contact lens and provides an indication of the presence of the oxidative disinfectant so that the disinfected lens can be safely and comfortably worn.

SUMMARY OF THE INVENTION

A new apparatus and method for disinfecting, and preferably cleaning, contact lenses has been discovered. The present system provides clear, positive and repeated indications of the presence of an oxidative disinfectant, preferably hydrogen peroxide, in the lens disinfecting medium. The indication of the presence of an oxidative disinfectant warns the lens wearer not to place the lens directly from the oxidative disinfectant-containing medium into the eye. Importantly, the means by which such indications are given is safe, preferably is useful when peroxidases, such as catalase, alone is used to destroy residual oxidative disinfectant, does not interfere with the disinfecting method and has no substantial detrimental effect on the lens being disinfected. In addition, the present indicator component preferably can be used many times, thus providing a cost effective approach to increasing the safety of contact lens disinfection. The present invention takes advantages of color differences in transition metal components to provide the indication or indications noted herein. Such color differences are particularly clear and distinct, which greatly adds to the usefulness of the present system. Moreover, the present invention effectively provides for immobilizing transition metal components so that concerns regarding potential toxicity to the eye and contact lens coloring are substantially reduced, or even eliminated.

In one broad aspect, the present invention is directed to an apparatus useful for disinfecting a contact lens which comprises a cup and a color indicator component. The cup is sized and adapted to hold a liquid medium containing an oxidative contact lens disinfectant, preferably hydrogen peroxide. The color indicator component is adapted to be located at least partially in this liquid medium in the cup, and acts to provide a color indication of the presence of the oxidative contact lens disinfectant in the liquid medium. The color indicator component comprises a transition metal component which is redox active, has an oxidized state and a reduced state, and is immobilized on a polymeric matrix material which is insoluble in the liquid medium. This matrix material is effective as a cation exchange medium to facilitate immobilizing the transition metal component. This polymeric matrix material is redox active and/or is a complexing agent for the transition metal component. The redox active polymeric matrix material in the reduced state is effective to at least facilitate reducing, preferably is effective to reduce, the transition metal component from the oxidized state. The complexing agent polymeric matrix material is effective to further facilitate immobilizing the transition metal component. The transition metal component is involved in providing the color indication of the presence of oxidative contact lens disinfectant in the liquid medium. Preferably, the oxidized transition metal component has a color which is different from the reduced transition metal component. The oxidized transition metal component is preferably effective to provide the color indication of the presence of /xidative contact lens disinfectant in the liquid medium.

In another broad aspect of the present invention, a method for disinfecting a contact lens is provided. This method comprises contacting a contact lens with a liquid medium containing an oxidative disinfectant, preferably hydrogen peroxide, at conditions effective to disinfect the contact lens. This contacting occurs in the presence of a color indicator component, as described herein, in an amount effective to provide a color indication of the presence, and preferably another color indication of the substantial absence, of the oxidative disinfectant in the liquid medium.

DETAILED DESCRIPTION OF THE INVENTION

The present invention is of value where /xidative disinfectants, in particular hydrogen peroxide, are used to disinfect all types of lenses, e.g., contact lenses, which are benefited by periodical disinfecting. Such lenses, e.g., conventional contact lenses, and preferably soft contact lenses, may be made of any suitable material or combination of materials and may have any suitable configuration not substantially deleteriously affected by such oxidative disinfectants.

Although any oxidative disinfectant which is able to effectively disinfect a contact lens and to oxidize the polymeric matrix material of the present invention may be employed, the much preferred oxidative disinfectant is hydrogen peroxide, especially aqueous solutions including hydrogen peroxide.

The present lens disinfecting apparatus includes a cup, preferably a substantially transparent cup, and a color indicator component.

The cup is sized and adapted to hold a liquid medium containing an oxidative contact lens disinfectant. Such cup may be made of any suitable material, such as, for example, glass, polymeric materials and the like, which are resistant to the action of the oxidative disinfectant and have no substantial detrimental effect on the disinfecting method, on the lens being disinfected or on the wearer of the disinfected lens. Examples of useful materials of construction include polymethylmethacrylate, polysulfone, acrylonitrile-butadiene-styrene terpolymers, polyphenylene oxide and the like. Preferably, the cup, or at least a portion thereof, is substantially transparent so that the color indication or indications of the present system can be easily visually monitored.

The present color indicator component is adapted to be located at least partially in the liquid medium in the cup. Such color indicator component is constructed of materials which have no substantial detrimental effect on the disinfecting method, on the lens being disinfected or on the wearer of the disinfected lens. The color indicator component is adapted to provide a color indication of the presence of the oxidative contact lens disinfectant in the liquid medium, and preferably a different color indication of the substantial absence of the /xidative disinfectant in the liquid medium.

The color indicator component comprises a transition metal component which is redox active, has an oxidized state and a reduced state and is immobilized on a polymeric matrix material. This polymeric matrix material is insoluble in the liquid, and remains insoluble in the liquid throughout the disinfecting processing, and is effective as a cation exchange medium, for example, is effective as a cation exchange resin, to facilitate immobilizing the transition metal component. In one embodiment, the polymeric matrix material is also redox active, and has an oxidized state and a reduced state and/or is a complexing agent for the transition metal component. The redox active polymeric matrix material in the reduced state is effective to at least facilitate reducing, preferably is effective to reduce, the transition metal component from the oxidized state to the reduced state. The complexing agent polymeric matrix material is effective to further facilitate immobilizing the transition metal component.

As used herein, the term "redox active" means that the component or material in question is capable of being oxidized from a reduced state to an oxidized state at the conditions present in the liquid medium containing oxidative contact lens disinfectant in the cup, and is capable of being reduced from the oxidized state to the reduced state at the conditions present in the liquid medium which is substantially free of oxidative contact lens disinfectant in the cup. Thus, the transition metal components, and, in /ne embodiment, the polymeric matrix materials, are present in an oxidized state in a oxidative contact lens disinfectant-containing liquid medium present in the cup. After all the oxidative contact lens disinfectant in this liquid medium has been destroyed, for example, chemically reduced or decomposed, the transition metal component and the redox active polymeric matrix material are present in the liquid medium in a reduced state.

Preferably, the transition metal component in the oxidized state has a color which is different from the transition metal component in the reduced state. In this embodiment, the oxidized transition metal component is effective to provide a color indication of the presence of oxidative contact lens disinfectant in the liquid medium.

The polymeric matrix material is insoluble, and remains insoluble, in the liquid medium used in the contact lens disinfecting, and is effective as a cation exchange medium to facilitate immobilizing the transition metal component. If the polymeric matrix material is redox active, the reduced polymeric matrix material is effective to at least facilitate reducing, and preferably is effective to reduce, the oxidized transition metal component. In this manner, the polymeric matrix material not only acts as a substrate for the immobilized transition metal component, but also at least assists in reducing the oxidized transition metal component.

This feature of the present invention is very advantageous in facilitating the repeated and effective use of the color indicator component. To illustrate, contact lenses are to be repeatedly subjected to disinfection. In each disinfection cycle, the color indicator component is to give a prompt and reliable indication of the presence, and preferably a prompt and reliable second indication of the substantial absence, of the oxidative contact lens disinfectant in the liquid medium. In order to give such indication or indications, the transition metal component should be capable of promptly and reliably cycling between the reduced state and the oxidized state in response to the presence or substantial absence of oxidative contact lens disinfectant in the liquid medium.

Certain non-redox active, non-complexing agent matrix materials have been considered to immobilize transition metal components as color indicators in contact lens disinfecting. A specific example of such a matrix polymer which has been considered is a perfluorosulfonic acid cation exchange resin sold by DuPont Company under the trademark Nafion. When ruthenium red is immobilized on such resin, an effective short term color indicator for oxidative contact lens disinfectant is obtained. However, after repeated uses (as would be the case in an actual real life situation), the response time for providing a color indication of the presence or substantial absence of oxidative contact lens disinfectant disadvantageously increases. For example, the response time for the transition metal component, e.g., ruthenium red, to change color to indicate the substantial absence of hydrogen peroxide contact lens disinfectant increases over time so that the user is given a "false positive" hydrogen peroxide indication and waits substantially longer than is necessary before removing the disinfected lens from the liquid medium. This increase in response time, which can cause user inconvenience and even increased risk of ocular damage, is not completely understood.

In addition, over time, the ruthenium content of the ruthenium/perfluorsulfonic acid cation exchange resin combination is reduced, thus further reducing the reliability of the color indications provided by such combination.

The present complexing agent polymeric matrix materials have been found to provide color indicator components in which the transition metal components are more effectively immobilized on the polymeric matrix material relative to a color indicator component employing only ion exchange to immobilize the transition metal component on the matrix material. This "complexing" or "coordination" function of the presently useful polymeric matrix materials has been found to effectively immobilize the transition metal component so that the color indicator component can be effectively repeatedly employed, that is over a relatively large number of disinfection cycles.

In a particularly useful embodiment, the polymeric matrix material is both redox active and a complexing agent for the transition metal component.

The presently useful "bifunctional" or "multifunctional" polymeric matrix materials effectively immobilize the transition metal components and provide color indicator components which exhibit rapid response times and reliable color indications even after many repeated uses.

In one embodiment, the polymeric matrix materials preferably include ligands, such as acid acting ligands, more preferably ligands other than sulfonic acid ligands, which yield color indicator components including transition metal components more strongly bonded or immobilized relative to a substantially identical color indicator component employing a polymeric matrix material with sulfonic acid ligands, for example, with perfluorosulfonic acid ligands.

Particularly useful acid acting ligands are selected from phosphorus-containing acid acting ligands, more preferably from phosphinic acid ligands, phosphonic acid ligands and mixtures thereof. An important advantage of using phosphorus-containing acid acting ligands, and preferably phosphinic/phosphonic acid ligands, is that the resulting polymeric matrix material is very effective in immobilizing the transition metal component so that the transition metal component remains immobilized even after repeated contact lens disinfecting cycles.

In one embodiment, the polymeric matrix material includes functionalities and/or ligands, hereinafter referred to singly and collectively as complexing groups, which complex with the transition metal component so as to further immobilize the transition metal component to the polymeric matrix material. Such complexing groups may be acid acting, preferably other than sulfonic acid groups, or non-acid acting; and may be redox active or redox inactive. Whether or not a specific functionality or ligand is a complexing group depends on the specific transition metal component involved. For example, amine functionalities are very effective complexing groups when transition metal components containing cobalt are being employed.

In one embodiment, the polymeric matrix material includes ligands, such as acid acting ligands, which are redox active, preferably bonded to a substantially non-redox active base polymer. Phosphinic acid ligands and phosphonic acid ligands are very useful redox active ligands.

Any suitable base polymer may be employed. The base polymer may include complexing groups. Examples of useful base polymers include polystyrene, polyvinylbenzene chloride, poly(pyrrol), polymers effective to chelate the transition metal component, polymers containing functional amine groups, polymeric derivatives thereof and the like and mixtures thereof. Examples of polymers which may chelate the transition metal component include iminodiacetate-agrose, iminodiacetate-polystyrene, and the like. Examples of polymers containing functional amine groups include poly(ethylenimine)cellulose, polyvinyl amine, polyvinyl imidazole, polyvinyl pyridine and the like. A particularly. useful base polymer comprises polystyrene. The ligands, for example, the redox active ligands, can be grafted or otherwise bonded to the base polymer using any suitable technique, many of which are conventional and known in the polymerization art. Such base polymer preferably is redox inactive.

Particularly useful bifunctional or multifunctional polymers as polymeric matrix materials in the present invention are those disclosed in: Alexandratos S. D., et al, "Dual Mechanism Bifunctional Polymers: Polystyrene-Based Ion-Exchange/Redox Resins", Macromolecules, 19, pp 280–287 (1986); and Alexandratos S. D., et at, "Synthesis and Characterization of Bifunctional Ion-Exchange/Coordination Resins", Macromolecules, 20, pp 11991–1196 (1987).

The transition metal component preferably comprises a metal selected from ruthenium, other platinum group metals, cobalt, copper, chromium and the like, and mixtures thereof. The transition metal component may be incorporated into the present color indicator component in any suitable form provided that such transition metal component functions as described herein. For example, the transition metal component may be selected from metal phthalocyanenes, metal poryphrines, and the like and mixtures thereof. Ruthenium red is a particularly useful transition metal component.

The transition metal component may be immobilized on the polymeric matrix material using any one or more of various ion exchange techniques, many of which are conventional and well known in the art. For example, an aqueous solution containing the transition metal component or precursor thereof may be contacted with the polymeric matrix material at conditions effective to ion exchange transition metal-containing ions onto the polymeric matrix material.

The amount of transition metal component immobilized on the polymeric matrix material is sufficient to provide the desired color indication or indications. For example, the transition metal component can be present in an amount in the range of about 0.005% or less to about 1 or about 2% or more of the total color indicator component, calculated as elemental transition metal.

The color indicator component, in use, is located in the liquid medium employed to disinfect a contact lens. Thus, the color indicator component can be secured in the inside, i.e., the interior space of the cup where the liquid medium is held, of the cup, may be adapted to move freely within the liquid medium in the cup, or may be an integral part of the cup.

For example, in the event the color indicator component is secured in the inside of the cup, it can comprise a band or other piece of material adhesively or otherwise secured to the cup. The color indicator component may be separate and apart from the cup such as in the form of a single disc or tablet, or a plurality of particles. In one embodiment, when the color indicator component is in the form of small particles, a retainer member, e.g., a screen element or ion permeable membrane, can be provided in the cup to keep the particles in place, and at the same time, allow the liquid medium in the cup to freely contact the particles.

The color indicator component may be integral with the cup. That is, for example, the cup can be made at least in part from the material used as the color indicator component. In one particularly useful embodiment, the material used to make the cup and the polymeric matrix material of the color indicator component are physically mixed together and processed, e.g., molded, to form the cup.

The present apparatus preferably further includes a basket assembly acting to hold a contact lens in the liquid medium in the cup. The color indicator component can be secured to the basket assembly or can be an integral part of the basket assembly. The basket assembly can be made of the same or different material or materials relative to the material or materials used to make the cup. Preferably, the basket assembly is substantially opaque, rather than transparent.

The cup may have a removable cover, which may be made of the same or different material or materials used to make the cup and which need not be transparent.

The liquid medium used in disinfecting a contact lens in the present invention preferably includes a disinfecting amount of oxidative disinfectant, preferably hydrogen peroxide. Preferably, a disinfecting amount of oxidative disinfectant means such amount as will reduce the microbial burden by one log in three hours. Still more preferably, the hydrogen peroxide concentration is such that the microbial load is reduced by one log order in one hour. Particularly preferred are those hydrogen peroxide concentrations which reduce the microbial load by one log unit in 10 minutes or less. Aqueous hydrogen peroxide solutions, preferably containing about 0.2% or about 0.5% to about 5% or about 6% of hydrogen peroxide (w/v), are known to be effective disinfecting solutions for contact lenses. These solutions are effective at killing bacteria and fungi which may be found on contact lenses. Typically, the amount of hydrogen peroxide used in the liquid medium is well in excess of that required to effectively disinfect a contact lens. Substantial excess hydrogen peroxide is used so that the lens disinfection can be completed in a reasonable period of time.

The liquid medium used is selected to have no substantial detrimental effect on the lens being treated and to allow, and preferably to even facilitate, the present lens treatment or treatments. The liquid medium is preferably aqueous-based. A particularly useful liquid aqueous medium is that derived from saline, e.g., a conventional saline solution. During the disinfecting contacting, it is preferred that the liquid aqueous medium have a pH in the range of about 3 to about 9, more preferably about 6 to about 8. The liquid medium, e.g., aqueous liquid medium, preferably includes a buffer which is present in an amount effective to maintain the pH of the liquid medium in the desired range. This buffer may be present in the liquid medium and/or may be introduced into the liquid medium. Among the suitable buffers or buffering agents which may be employed are those which are conventionally used in contact lens care products. Examples of useful buffers include those with carbonate functionalities, bicarbonate functionalities, phosphate functionalities, borate functionalities, and the like and mixtures thereof. The buffers may be alkali metal and alkaline earth metal salts, in particular sodium and potassium.

In one embodiment, an oxidative disinfectant destroying component, hereinafter referred to as an ODDC, is included in a solid composition, e.g., a tablet, capsule, one or more solid particles and the like, which is preferably introduced into the liquid medium about the same time as the lens to be disinfected is introduced into the liquid medium. Such solid compositions include one or more ODDCs in an amount effective to destroy all the residual oxidative disinfectant remaining in the liquid medium after the lens has been disinfected and preferably to reduce the polymer matrix material and the transition metal component of the color indicator component to the reduced states.

Thus, such preferred solid compositions, which are preferably initially contacted with the oxidative disinfectant-containing liquid medium at substantially the same time as is the lens to be disinfected, allow for effective lens disinfection and, in addition, effectively destroy the residual oxidative disinfectant remaining in the oxidative disinfectant-containing liquid medium so that the disinfected lens can be removed from the liquid medium and placed directly into the eye for safe and comfortable wear. If, as is preferred, such compositions also reduce the polymeric matrix material of the Color indicator component to the reduced state, the transition metal component of the color indicator component is also reduced and a second color indication of the substantial absence of the oxidative disinfectant is provided while the contact lens remains in the liquid medium, thus giving added assurance to the lens wearer that it is safe to remove the lens from the liquid medium and to wear the disinfected lens. Such preferred compositions may be present in the form of at least one item, e.g., tablet, capsule, one or more solid particles and the like, which includes a coated portion, e.g., a core such as a core tablet, and a barrier component. The coated portion includes the ODDC or ODDCs. The barrier component acts to delay the release of the ODDC or ODDCs from the coated portion into the liquid medium for a period of time, preferably sufficient to allow the lens to be disinfected. Preferably, the barrier coating substantially surrounds the coated portion.

Any suitable ODDC may be employed provided such ODDC has no substantial detrimental effect on the present system, on the disinfected lens or on the wearer of the disinfected lens. Among the useful ODDC are oxidative disinfectant reducing agents, peroxidases (meaning to include therein catalase) and mixtures thereof. One important advantage of the present system is that when peroxidases are used to destroy the oxidative disinfectant, such peroxidases preferably also reduce the polymeric matrix material, so that no other reducing agent need be included. In certain other redox systems, the peroxidase used are substantially ineffective in providing a reduced state redox material. The need to use a separate reducing agent is a major disadvantage of such other systems.

Examples of the oxidative disinfectant reducing agents which are useful in the present invention are alkali metal, in particular sodium, thiosulfates; thiourea; alkali metal, in particular sodium, formiates; pyruvic acid and salts of pyruvic acid, N-acetylcysteine, ene-diol compounds, e.g., ascorbic acid compounds, reductive acid compounds, isoascorbic acid compounds, glyoxylic acid compounds, squaric acid compounds, dihydroxymaleic acid compounds, dihydroxyfumaric acid compounds and mixtures thereof. Typical examples of the foregoing ene-diol compounds are the acids themselves, e.g., ascorbic acid, ophthalmically acceptable salts of such acids, e.g., sodium ascorbate, ophthalmically acceptable esters of such acids, e.g., ascorbic palmirate and any other ophthalmically acceptable derivatives of such acids, e.g., that retain the ene-diol molecular structure, mixtures thereof and the like. A particularly useful peroxidase is catalase. The peroxidases, and especially catalase, are very beneficial in the present invention since such ODDCs are effective to substantially eliminate hydrogen peroxide from a liquid medium in a reasonable period of time, e.g., on the order of about 1 minute to about 12 hours, preferably about 5 minutes to about 1 hour, after the ODDC is initially released into the liquid medium.

The amount of ODDC employed is preferably sufficient to destroy all the oxidative disinfectant present in the liquid medium into which the ODDC is placed and preferably reduce the polymeric matrix material to the reduced state. Excess ODDC may be employed. Very large excesses of ODDC are to be avoided since the ODDC itself may cause problems with the disinfected lens and/or the ability to safely and comfortably wear such disinfected lens, When catalase is employed a part of the ODDC, it is preferably present in an amount of about 100 to about 1000, more preferably about 150 to about 700 units of catalase activity per milliliter of liquid medium. For example, an especially useful amount of catalase for use in an aqueous solution containing about 3% (w/v) hydrogen peroxide is about 520 units of catalase activity/ml of solution.

The delayed release of the ODDC or ODDCs into the liquid medium may be accomplished in any one of many suitable ways, a number of which are conventional and well known in the art. For example, the barrier, component, e.g., coating, may be provided by coating a core tablet, or other particle, containing the ODDC or ODDCs with a slow dissolving coating material, which may ultimately be completely or only partially soluble in the liquid medium, or by including the ODDC or ODDCs in a matrix from which it may be slowly leached. Also, the matrix may be coated with a slow dissolving material so that the start of the slow release is delayed. The delayed release form of the ODDC or ODDCs is preferably such that substantially no release occurs during a delay period followed by rapid and substantially complete release of the ODDC or ODDCs at the end of the delay period. Such a result may be obtained by coating the ODDC or ODDCs with a slow dissolving coating.

Barrier components suitable as either coatings or as matrices, include water soluble vinyl polymers, such as polyvinylpyrrolidone, polyvinylalcohol and polyethyleneglycol; water soluble proteins; polysaccharide and cellulose derivatives, such as methyl cellulose, hydroxypropylmethyl cellulose, sodium carboxymethyl cellulose; alginic acid and its salts and other derivatives; and the like and mixtures thereof. Mixtures of the above materials may be used.

The amount of barrier component used is not critical in the present invention provided that such barrier component functions as described herein. The barrier component or components may suitably be present in the range of about 1% to about 20% or more, based on the weight of the ODDC or ODDCs.

The solid compositions may be produced using any one of many suitable methods, a number of which are conventional and well known in the art.

The solid compositions may include other components, for example, fillers, binders, tonicity agents, contact lens conditioning/wetting agents, buffering agents, lubricating agents and the like. Each of these components may be present, if at all, in an amount effective to perform its designated function or functions. Examples of each of these types of components are conventional and well known in the art. Therefore, a detailed description of such components is not presented here.

In a particularly useful embodiment, the contact lens may be subjected to the action of at least one enzyme effective to remove debris from a contact lens. Among the types of debris that form on contact lens during normal use are protein-based debris, mucin-based debris, lipid-based debris and carbohydrate-based debris. One or more types of debris may be present on a single contact lens.

The enzyme employed may be selected from peroxide-active enzymes which are conventionally employed in the enzymatic cleaning of contact lenses. For example, many of the enzymes disclosed in Huth et al U.S. Pat. No. 3,910,296 are useful in the present invention. These patents are incorporated in their entirety by reference herein. Among the useful enzymes are those selected from proteolytic enzymes, lipases and mixtures thereof.

Preferred proteolytic enzymes are those which are substantially free of sulfhydryl groups or disulfide bonds, whose presence may react with the active oxygen of the disinfectant to the detriment of the activity of the enzyme. Metallo-proteases, those enzymes which contain a divalent metal ion such as calcium, magnesium or zinc bound to the protein, may also be used.

A more preferred group of proteolytic enzymes are the serine proteases, particularly those derived from Bacillus and Streptomyces bacteria and Asperigillus molds. Within this grouping, the still more preferred enzymes are the derived alkaline proteases generically called subtilisin enzymes. Reference is made to Deayl, L., Moser, P. W. and Wildi. B. S., "Proteases of the Genus Bacillus. II Alkaline Proteases", Biotechnology and Bioengineering, Vol. XII, pp 213–249 (1970) and Keay, L. and Moser, P. W., "Differentiation of Alkaline Proteases form Bacillus Species" Biochemical and Biophysical Research Comm., Vol 34, No. 5, pp 600–604, (1969).

The subtilisin enzymes are broken down into two sub-classes, subtilisin A and subtilisin B. In the subtilisin A grouping are enzymes derived from such species as *B. subtills, B. licheniformis* and *B. pumilis*. Organisms in this sub-class produce little or no neutral protease or amylase. The subtilisin B sub-class is made up of enzymes from such organisms a *B. subtilis, B. subtilis var. amylosacchariticus, B. amyloliquefaciens* and *B. subtilis* NRRL B3411. These organisms produce neutral proteases and amylases on a level about comparable to their alkaline protease production. One or more enzymes from the subtilisin A sub-class are particularly useful.

In addition other preferred enzymes are, for example, pancreatin, trypsin, collaginase, keratinase, carboxylase, aminopeptidase, elastase, and aspergillo-peptidase A and B, pronase E (from *S. griseus*) and dispase (from *Bacillus polymyxa*).

If such an enzyme or enzymes are employed, an effective amount is preferably used. Such amount will be that amount which effects removal in a reasonable time (for example overnight) of substantially all of at least one type of debris from a lens due to normal wear. This standard is stated with reference to contact lens wearers with a history of normal pattern of lens debris accretion, not the very small group who may at one time or another have a significantly increased rate of debris accretion such that cleaning is recommended every day, or every two or three days.

The amount of enzyme required to make an effective cleaner will depend on several factors, including the inherent activity of the enzyme, and the extent of its interaction with the hydrogen peroxide present.

As a basic yardstick, the working solution should contain sufficient enzyme to provide about 0.001 to about 3 Anson units of activity, preferably about 0.01 to about 1 Anson units of activity, preferably about 0.01 to about 1 Anson units, per single lens treatment. Higher or lower amounts may be used.

Enzyme activity is pH dependent so for any given enzyme, there is a particular pH range in which that enzyme will function best. The determination of such range can readily be done by known techniques.

Solid compositions which include such lens cleaning enzymes may be structured to release the enzyme, into the liquid medium which contacts the composition, at any time relative to the other component or components of the composition provided that the released enzyme is effective at the conditions present in the liquid medium to perform the cleaning function, as described herein. In one particularly useful embodiment, the cleaning enzyme is released into the liquid medium substantially immediately upon introducing the solid composition into the liquid medium.

In the event that a debris removing enzyme is present, the contact lens in the liquid medium is effectively cleaned of such debris. This cleaning action can occur before the lens is disinfected, at the time the lens is being disinfected or after the lens is disinfected.

The disinfecting contacting preferably occurs at a temperature to maintain the liquid medium substantially liquid. It is preferred that the contacting temperature be in the range of about 0° C. to about 100° C., and more preferably in the range of about 10° C. to about 60° C. and still more preferably in the range of about 15° C. to about 30° C. Contacting at or about ambient temperature is very convenient and useful. The contacting preferably occurs for a time to substantially completely disinfect the lens being treated. Such contacting times can be in the range of about 1 minute to about 12 hours or more.

After such contacting, the liquid medium preferably includes substantially no residual, oxidative disinfectant and the disinfected lens can be removed from this liquid medium and placed directly into the eye for safe and comfortable wear. However, if the liquid medium includes one or more "cleaning" enzymes, it is preferred to rinse the disinfected lens, e.g., with saline, to free the lens of such enzyme prior to placing the disinfected lens into the eye.

BRIEF DESCRIPTION OF THE DRAWINGS

FIG. 1 is a front elevation view, partly in cross-section, illustrating one embodiment of the present apparatus.

FIG. 2 is a front elevation view, partly in cross-section, illustrating another embodiment of the present apparatus.

FIG. 3 is a front elevation view, partly in cross-section, illustrating an additional embodiment of the present apparatus.

FIG. 4 is a front elevation view, partly in cross-section, illustrating a further embodiment of the present apparatus.

FIG. 5 is a front elevation view, partly in cross-section, illustrating another embodiment of the lens basket of the present apparatus.

DETAILED DESCRIPTION OF THE DRAWINGS

Referring now to FIG. 1, a lens disinfection apparatus, shown generally at 10, include a lens container 12, a cover 14, and a lens basket 16.

Lens container 12 is made of a transparent, thermoplastic polymeric material, such as polymethylmethacrylate, and is made, e.g., molded using conventional techniques, as a single unit. Lens container 12 includes a bottom wall 18 and a sidewall 20. The upper portion 22 of sidewall 20 is flared outwardly. The top 24 of sidewall 20 includes a threaded outer surface 26. The cross-section of lens container 12 parallel to bottom wall 18 is generally circular. Lens container 12 defines an interior space 28 in which is placed a hydrogen peroxide-containing aqueous liquid medium.

Within interior space 28 and secured to the inner surface 30 of sidewall 20 is a color indicator band 32, which is made of a water-insoluble polystyrene containing phosphinic acid ligands and to which is bonded or complexed ruthenium ions. The ruthenium content of the color indicator band 32, which is immobilized on the phosphinic acid ligand-containing polystyrene using conventional ion exchange processing, constitutes about 0.01% by weight of the indicator bond, calculated as elemental ruthenium. The entire color indicator band 32 is substantially insoluble in the liquid medium. The ruthenium (ruthenium +4) is yellow in color in the presence of hydrogen peroxide.

The color indicator band 32 is generally right circular cylindrical in configuration and defines a through space 34 through which liquid can freely &low. Band 32 can be adhesively secured to inner surface 30 and is conveniently placed in interior space 28 to be completely submerged in the hydrogen peroxide-containing aqueous liquid medium during contact lens disinfecting.

Cover 14 includes a top wall 36 and a downwardly depending sidewall 38. Cover 14 is made of a nontransparent, thermoplastic polymeric material, such as polyphenylene oxide. Top wall 36 is generally circular and the cross-section of sidewall 38 parallel to top wall 36 is generally circular. Sidewall 38 includes a threaded inner surface 40 the threads of which matingly engage the threads of threaded outer surface 26 to secure cover 14 to lens container 12. Cover 14 also includes a central, circular hollow projection 42 which, extends downwardly into lens container 12 when cover 14 is secured to lens container 12. An attachment element 44 of lens basket 16 is secured, e.g., by adhesive, interference fitting and the like, in the hollow space defined by projection 42. In this manner, lens basket 16 is secured to cover 14. A pair of foamed polymeric sealing elements 46 and 48 are fitted on the underside of cover 14 around projection 42 and act to provide a substantially liquid tight seal when cover 14 is secured to lens container 12.

Lens basket 16 is made of a non-transparent, thermoplastic polymeric material, such as polyphenylene oxide. Like lens container 12 and cover 14, lens basket 16 can be made, e.g., molded, using conventional techniques. As noted above, lens basket 16 includes attachment element 44 which is secured to cover 14. Extending downwardly from attachment element 44 is basket body 50 which includes left lens mount 52 and right lens mount 54. Basket body 50 includes a series of through holes (not shown) which allow liquid to freely pass through the basket body.

A left basket cover 56 and a right basket cover 58 are both hingedly secured to basket body 50 and are structured to be "snapped" closed around left lens mount 52 and right lens mount 54, respectively, as desired, to form a left lens compartment 60 and a right lens compartment 62, respectively. The basket covers 56 and 58 are made separately from the other components of the lens basket 16. Each of the basket covers 56 and 58 include a series of through holes 7hich allow liquid to flow freely through. However, these through holes are sized so that the contact lenses in lens compartments 60 and 62 cannot be removed when the lens covers 56 and 58 are closed. Left basket cover 56 may be marked with a "L" to indicate that it is to be used with the left contact lens. Similarly, the right basket cover 58 may be marked with a "R" to indicate that it is to be used with the right contact lens.

Lens disinfection apparatus 10 may be used as follows with cover 14 removed from lens container 12, the contact lenses to be disinfected are placed on the appropriate left and right lens mounts 52 and 54, respectively and the left and right basket covers 56 and 58 are snapped closed.

A quantity, e.g., about 10 ml, of a 3% (w/v) hydrogen peroxide aqueous solution is placed in the interior space 28 of lens container 12 and completely immerses band 32. After the hydrogen peroxide solution is added, the band 32 is yellow in color, indicating the presence of hydrogen peroxide in the interior space 28. Cover 14 is applied to lens container 12 and secured in place. The contact lenses in lens compartments 60 and 62 are completely submerged in the hydrogen peroxide solution. Over a period of time, e.g., on the order of about 4 hours, the contact lenses are effectively disinfected. However, the band 32 remains yellow indicating the continued presence of hydrogen peroxide.

At this point, the cover 14 is removed from the lens container 12 and a tablet containing sufficient catalase to destroy the remaining hydrogen peroxide in the solution and to provide the polymeric matrix material in the band 32 in a reduced state is added to the solution and the cover 14 is again secured to the lens container 12.

After another period of time, e.g., about one (1) hour, the band 32 is red in color, indicating that the ruthenium has been reduced (to ruthenium +3) and that the solution in interior space 28 contains substantially no hydrogen peroxide. The contact lens can then be removed from the lens compartments 60 and 62, rinsed with saline solution, and placed directly into the wearer's eyes for safe and comfortable wear.

Several alternative approaches to disinfecting, and cleaning, contact lenses using apparatus 10 are possible. For example, the catalase with a delayed release coating can be added to the hydrogen peroxide-containing solution at substantially the same time the contact lenses are first contacted with this solution. The band 32 is yellow in color indicating the presence of hydrogen peroxide. After a period of time, the delayed release coating dissolves releasing the catalase into the solution. After another period of time, the band 32 is red in color indicating that the solution in interior space 28 includes substantially no hydrogen peroxide. The disinfected contact lenses can be rinsed with saline solution and placed in the wearer's eyes for safe and comfortable wear.

Another alternative involves coating the delayed release coating with a hydrogen peroxide active enzyme, e.g., subtilisin A enzyme, in an amount effective to remove at least one type of debris, e.g., proteinaceous debris. In this embodiment, the enzyme/catalase combination with the delayed release coating can be added to the hydrogen peroxide-containing solution at substantially the same time the contact lenses are first contacted with this solution. The band 32 is yellow in color indicating the presence of hydrogen peroxide. After a period of time, during which the hydrogen peroxide-active enzyme removes proteinaceous debris from the contact lenses and the contact lenses are effectively disinfected, the delayed release coating release the catalase into the solution. After another period of time, the band 32 is red in color, indicating that the solution interior space 28 includes substantially no hydrogen peroxide. The cleaned and disinfected contact lenses can be rinsed with saline solution to remove the subtilisin A enzyme and placed in the wearer's eyes for safe and comfortable wear.

FIG. 2 illustrates another embodiment of the present invention. Except as expressly stated elsewhere herein, this lens disinfection apparatus, shown generally at 110, is constructed and functions in a manner similar to lens disinfection apparatus 10. Components of apparatus 100 which correspond to components of apparatus 10 are indicated by corresponding reference numerals increased by 100.

One primary difference between apparatus 100 and apparatus 10 is that apparatus 110 does not include a color indicator band, such as color indicator band 32. Instead apparatus 110 includes a color indicator disc 70, which is made of the same material, as is color indicator band 32. Color indicator disc 70 is included in the interior space 128 of apparatus 110 during the time the contact lenses in lens basket 116 are being disinfected or cleaned and disinfected.

Color indicator disc 710 is yellow in color, indicating the presence of hydrogen peroxide, and is red in color, indicating the substantial absence of hydrogen peroxide.

FIG. 3 illustrates an additional embodiment of the present invention. Except as expressly stated elsewhere herein, this lens disinfection apparatus, shown generally at 210, is constructed and functions in a manner similar to lens disinfection apparatus 10. Components of apparatus 210 which correspond to components of apparatus 10 are indicated by corresponding reference numerals increased by 200.

One primary difference between apparatus 210 and apparatus 10 is that apparatus 210 does not include a color indicator band, such as color indicator band 32. Instead, apparatus 210 includes a plurality of color indicator beads 72 which are located at or near the bottom of interior space 228. A screen insert 74 is fitted within the inner wall 230 of lens container 212. Screen insert 74 includes a plurality of holes sized so as to allow free access of the liquid material inside inner space 228 across screen insert 74. At the same time, these holes are insufficiently large to allow the color indicator beads 72 to escape the compartment 78 defined by screen insert 74 and the bottom portion of lens container 212. In an alternate embodiment, the color indicator beads 72 may be located along the sidewall of interior space 228 within an appropriately sized and configured screen element which functions in a manner similar to screen insert 74.

Color indicator beads 72 are made of the same material as color indicator band 32. Color indicator beads 72 are included in the space 78 defined by screen insert 74 and the bottom portion of lens container 212 during the time the contact lenses are being disinfected or cleaned and disinfected. Color indicator beads 72 are yellow in color, indicating the presence of hydrogen peroxide, and are red in color, indicating the substantial absence of hydrogen peroxide.

If desired, the screen insert 74 can be removed from lens container 212 to replace color indicator beads 72. One important advantage of lens disinfection apparatus 210, for example relative to lens disinfection apparatus 110, is that the color indicator beads 72 remain in place between uses of apparatus 210 and are, therefore, not prone to being lost. The color indicator disc 70 of lens disinfection apparatus 100 can be removed between uses and become lost.

FIG. 4 illustrates a further embodiment of the present invention. Except as expressly stated elsewhere herein, the lens disinfection apparatus, shown generally at 310, is constructed and functions in a manner similar to lens disinfection apparatus 10. Components of apparatus 310 which correspond to components of apparatus 10 are indicated by corresponding reference numerals increased by 300.

One primary difference between apparatus 310 and apparatus 10 is that apparatus 310 does not include a color indicator band, such as color indicator band 32. Instead, apparatus 310 is provided with a color indicating lens container 80 which is made of a physical mixture of polymethylmethacrylate and the ruthenium-containing polymer described previously with regard to apparatus 10. This physical mixture of polymers is combined and then used to fabricate lens container 80. Sufficient ruthenium-containing polymer is included so that the lens container has a yellow tint in the presence of hydrogen peroxide.

Lens container 80 includes an interior space 82 in which is placed a hydrogen peroxide-containing aqueous liquid medium.

Lens container 80 is configured substantially similarly to lens container 12. Lens container 80 has a yellow tint, indicating the presence of hydrogen peroxide in the aqueous liquid medium in interior space 82, and a reddish tint, indicating the substantial absence of hydrogen peroxide in such aqueous liquid medium.

FIG. 5 illustrates another embodiment of the lens basket of the present invention. Except as expressly stated elsewhere herein, this lens basket, shown generally at 416, is constructed and functions in a manner similar to lens basket 16. Components of lens basket 416 which correspond to components of lens basket 16 are indicated by corresponding reference numerals increased by 400.

One primary difference between lens basket 416 and lens basket 16 is the material of construction used in lens basket 416. Thus, lens basket 416 is made of a physical mixture of polyphenylene oxide and the ruthenium-containing polymer described with regard to lens disinfection apparatus 10. Sufficient ruthenium-containing polymer included so that the entire lens basket 416 is yellow in color in the presence of hydrogen peroxide.

Lens basket 416 can be effectively utilized as both a lens basket and a color indicator for the presence of hydrogen peroxide. A particularly useful embodiment would involve replacing lens basket 116 with lens basket 416 in lens disinfection apparatus 110 and removing color indicator disc 70. In this embodiment, lens basket 416 is yellow in color indicating the presence of hydrogen peroxide, and is red in color, indicating the substantial absence of hydrogen peroxide.

The following non-limiting examples illustrate certain aspects of the present invention.

EXAMPLE 1

This example illustrates a lens cleaning/disinfecting embodiment of the present invention, with specific reference to FIG. 3.

About 1 g of beads 72 made of the water insoluble ruthenium-containing polymer described above with reference to the drawings is placed in the bottom portion 78 of interior space 228.

A pair of protein-based debris laden contact lenses are placed in lens basket 216. 10 ml of a saline solution containing 3% (w/v) of $H_2O_2$ and 0.3% by weight of boric acid is added to the interior space 228, and the lens basket 216 is positioned so that the contact lenses are completely submerged in the solution in lens container 212. The pH of this solution is about 7.5. At this point the beads 72 are yellow in color.

A layered, delayed release tablet is dropped into the solution in lens container 212. The center core of the tablet includes 2.0 mg of crystalline catalase. The outer layer of the tablet includes 0.4 mg of subtilisin A enzyme. A delayed release layer between the inner layer and the outer layer is structured and designed to dissolve sufficiently in two hours after being exposed to the solution in the lens container 212 to release the catalase into the solution.

Upon being dropped into the solution, the outer layer of the tablet dissolves to release the subtilisin A into the solution. The enzyme in the outer layer begins to attack and remove the protein-based debris on the lenses. Substantially all of the protein-based debris is removed from the lenses. In addition, the contact lenses are effectively disinfected. Two hours after the layered tablet is first dropped into the solution, the catalase is released into the solution and destroys the residual hydrogen peroxide in the solution and reduces the polymer in the beads 72 to a reduced state. The beads 72 turn red in color. Upon seeing the beads 72, the lens wearer removes the cleaned/disinfected lenses from the solution, rinses them with physiological saline solution to remove the subtilisin A enzyme, and places them in his/her eyes. It is found that the contact lenses are effectively disinfected and cleaned of protein-based debris. The lens wearer experiences no discomfort or eye irritation from wearing the disinfected and cleaned contact lenses.

This contact lens disinfection cycle is repeated many times, for example, on the order of about 30 or about 100 or more times. In each such cycle, clear and reliable color indications of the presence and substantial absence of hydrogen peroxide contact lens disinfectant are given. Substantially no detrimental increases in response time (time for the beads 72 to change color) are observed. In addition, the beads 72 retain substantially all of the ruthenium present on the beads after the first disinfection cycle.

EXAMPLES 2 AND 3

Two samples of beads are prepared using conventional ion exchange techniques. One sample of beads, Sample A, is similar to the beads 72 identified in Example 1. The other sample of beads, Sample B, includes a perfluorsulfonic acid cation exchange resin sold by DuPont Company under the Trademark Nafion in place of the phosphinic acid ligand-containing polystyrene.

Both samples are repeatedly cycled between unit doses of a commercially available hydrogen peroxide-containing contact lens disinfectant sold by Allergan, Inc. under the trademark LENS PLUS Oxysept 1 and unit doses of a commercially available catalase-containing neutralizing solution (for hydrogen peroxide contact lens disinfectant) sold by Allergan, Inc. under the trademark LENS PLUS Oxysept 2.

Both Samples A and B initially are effective color indicators of the presence and substantial absence of hydrogen peroxide. Thus, initially, both samples are yellow in the hydrogen peroxide solutions and rapidly turn red when placed in the catalase solutions. However, over time, the response time of Sample B to change from yellow to red after being placed in the catalase solution is observed to increase. No comparable increase in response time is seen with Sample A. In addition, over time, some of the ruthenium is lost from the Sample B beads. No comparable loss of ruthenium is observed with Sample A.

The increase in response time is disadvantageous because the user is given a "false positive" indication of the presence of hydrogen peroxide. Because this indication is false, the user may come to disregard the yellow color as a true indication of the presence of hydrogen peroxide and place a hydrogen peroxide-contaminated lens in his/her eye, causing discomfort, irritation or even eye damage. In addition, the ruthenium lost from the Sample B beads may detrimentally affect, e.g., color, the lens being disinfected.

Sample A, in accordance with the present invention, after repeated cycles continues to provide rapid and reliable indications of the presence and substantial absence of hydrogen peroxide with no substantial loss of ruthenium.

While this invention has been described with respect to various specific examples and embodiments, it is to be understood that the invention is not limited thereto and that it can be variously practiced within the scope of the following claims.

What is claimed is:

1. A method for disinfecting a contact lens comprising:
contacting a contact lens with a liquid medium containing a disinfecting amount of an oxidative contact lens disinfectant at conditions to effectively disinfect said contact lens, said contacting occurring in the presence of a color indicator component adapted to provide a color indication of the presence of said oxidative contact lens disinfectant in said liquid medium, said color indicator component comprising a transition metal component which is present in an amount effective to provide said color indication, is redox active, has an oxidized state and a reduced state and is immobilized on a polymeric matrix material which is and remains insoluble in said liquid medium and is present in an amount effective to act as a cation exchange medium to facilitate immobilizing said transition metal component, said polymeric matrix material being (1) redox active at said conditions and having an oxidized state and a reduced state, provided that said polymeric matrix material in said reduced state is effective to at least facilitate reducing said transition metal component from said oxidized state; and (2) a complexing agent at said conditions for said transition metal component, wherein said polymeric matrix material includes phosphorus-containing acid acting ligands and said transition metal component is more strongly immobilized on said polymeric matrix material relative to a substantially identical polymeric matrix material including sulfonic acid ligands instead of said phosphorus-containing acid acting ligands.

2. The method of claim 1 wherein said oxidative contact lens disinfectant is hydrogen peroxide, and said polymeric matrix material in said reduced state is effective to reduce said transition metal component from said oxidized state.

3. The method of claim 1 wherein said transition metal component in said oxidized state has a color which is different from said transition metal component in said reduced state, and said transition metal component in said oxidized state is effective to provide said color indication of the presence of said oxidative contact lens disinfectant in said liquid medium.

4. The method of claim 1 which further comprises destroying said oxidative contact lens disinfectant so as to provide a substantially oxidative contact lens disinfectant-free liquid medium and to provide said polymeric matrix material in said reduced state, said transition metal component being reduced to said reduced state which provides a different color indication of the substantial absence of said oxidative contact lens disinfectant in said substantially oxidative contact lens disinfectant-free liquid medium.

5. The method of claim 4 wherein a peroxidase component is present during said destroying step in an amount effective to provide said substantially oxidative contact lens disinfectant-free liquid medium and said polymeric matrix material in said reduced state.

6. The method of claim 1 wherein said transition metal component in said reduced state is effective to provide a different color indication of the substantial absence of said oxidative contact lens disinfectant in said substantially oxidative contact lens disinfectant-free liquid medium.

7. The method of claim 1 wherein said polymeric matrix material comprises a polymer selected from the group consisting of polystyrene, polyvinylbenzene chloride, polymeric derivatives thereof and mixtures thereof.

8. The method of claims 1 wherein said polymeric matrix material includes a base polymer to which said phosphorus-containing acid acting ligands are bound.

9. The method of claim 1 wherein said transition metal component comprises a metal selected from the group consisting of ruthenium, other platinum group metals, copper, cobalt, chromium and mixtures thereof.

10. The method of claim 4 wherein catalase is present during said destroying step in an amount effective to provide said substantially oxidative contact lens disinfectant-free liquid medium and said polymeric matrix material in said reduced state.

11. The method of claim 4 wherein said contacting and said destroying steps are repeatedly conducted in the presence of said color indicator component, and said color indicator component has a more constant color change response time after being used repeatedly in said contacting and said destroying steps relative to a substantially identical color indicator component including sulfonic acid ligands instead of said phosphorus-containing acid acting ligands.

12. The method of claim 11 wherein said polymeric matrix material comprises a polymer selected from the group consisting of polystyrene, polyvinylbenzene chloride, polymeric derivatives thereof and mixtures thereof.

13. The method of claim 11 wherein said transition metal component comprises a metal selected from the group consisting of ruthenium, other platinum group metals, copper, cobalt, chromium and mixtures thereof.

14. The method of claim 11 wherein said oxidative contact lens disinfectant is hydrogen peroxide, and catalase is present during said destroying step to provide said substantially oxidative contact lens disinfectant-free liquid medium and said polymeric matrix material in said reduced state.

15. The method of claim 1 wherein said phosphorus-containing acid acting ligands are phosphinic acid ligands.

* * * * *